(12) United States Patent
Hemmendorff

(10) Patent No.: US 7,545,908 B2
(45) Date of Patent: Jun. 9, 2009

(54) METHOD AND ARRANGEMENT RELATING TO X-RAY IMAGING

(75) Inventor: Magnus Hemmendorff, Arsta (SE)

(73) Assignee: Sectra Mamea AB, Kista (SE)

( * ) Notice: Subject to any disclaimer, the term of this patent is extended or adjusted under 35 U.S.C. 154(b) by 0 days.

(21) Appl. No.: 11/669,861

(22) Filed: Jan. 31, 2007

(65) Prior Publication Data

US 2008/0181360 A1    Jul. 31, 2008

(51) Int. Cl.
*A61B 6/04* (2006.01)
(52) U.S. Cl. .......................................... 378/37; 378/205
(58) Field of Classification Search .................... 378/37, 378/195–196, 62, 205, 197, 4
See application file for complete search history.

(56) References Cited

U.S. PATENT DOCUMENTS 6,744,848 B2 *   6/2004   Stanton et al. ................. 378/55
2004/0202279 A1 *  10/2004   Besson et al. .................. 378/37

* cited by examiner

*Primary Examiner*—Hoon Song
(74) *Attorney, Agent, or Firm*—Fox Rothschild, LLP; Peter J. Butch, III

(57) ABSTRACT

To enhance results of an x-ray apparatus the invention relates to an apparatus for three-dimensional imaging of a human breast comprising a reconstruction means for reconstruction of a three-dimensional image volume, a compression paddle for holding said breast, an actuator for controlling the position of said compression paddle, and a position gauge for measurement of the position of said compression paddle. The reconstruction means is operatively arranged to receive signals, corresponding to measurements by said position gauge, from said position gauge and constrain the boundary of said image volume based on said received signal.

26 Claims, 2 Drawing Sheets

METHOD AND ARRANGEMENT RELATING TO X-RAY IMAGING

TECHNICAL FIELD OF THE INVENTION

Figure 1:
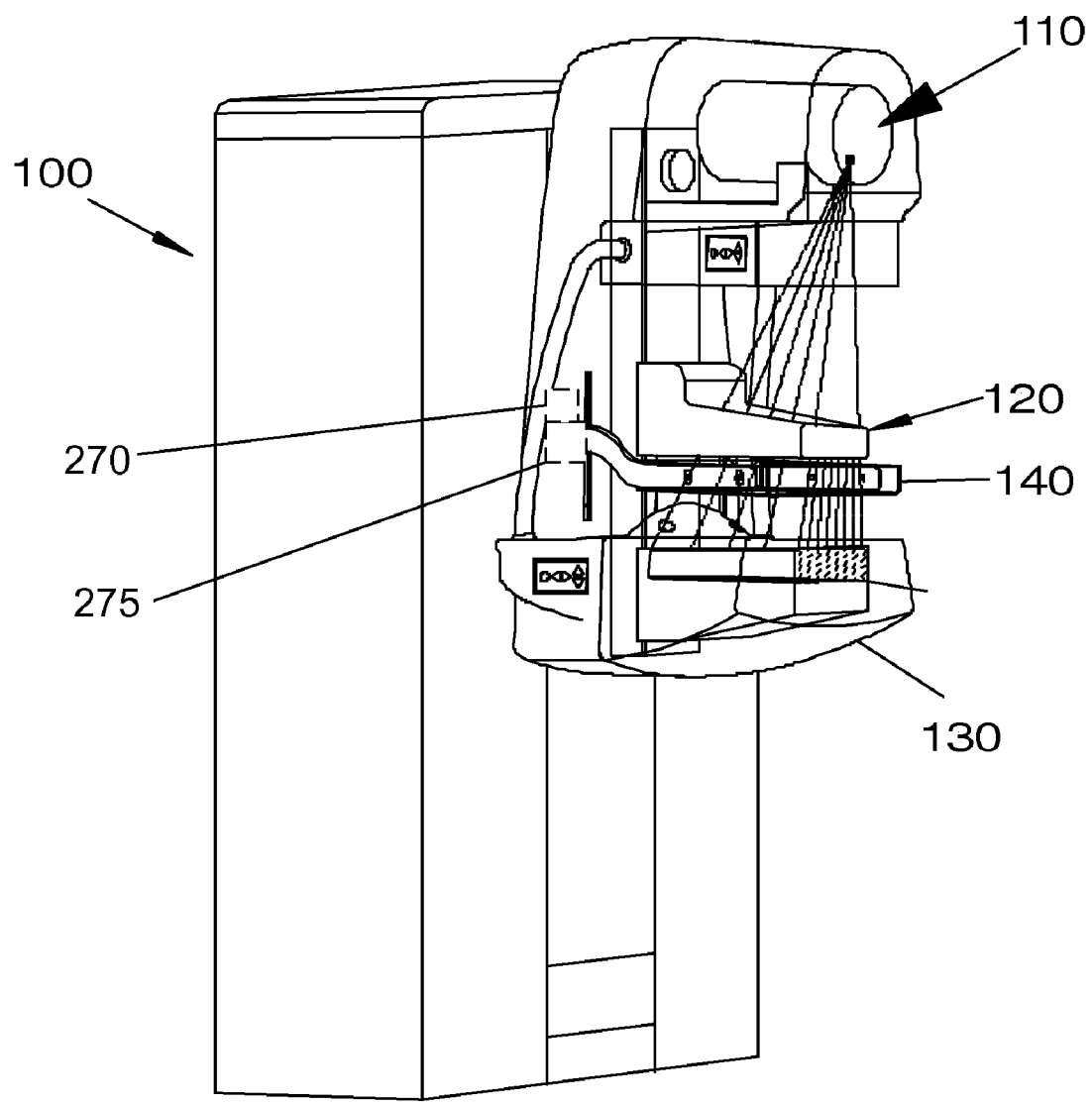

The present invention relates to a method and arrangement in X-ray imaging, in particular three-dimensional imaging, and more especially tomosynthesis.

BACKGROUND OF THE INVENTION

Tomosynthesis is used to create a three-dimensional image volume of a person's body part, e.g. her breast, or an object, using X-rays. Currently, tomosynthesis breast imaging is available only for research purposes, but an increasing number of market analysts believe it will become more widely used than conventional two-dimensional mammography. Tomosynthesis is essentially a limited form of Computed Tomography or CT. Normally, several projection images, e.g. 5 or 30, are acquired in a range of different angles, e.g. −10 to +10 degrees. Each projection image is essentially a conventional 2-dimensional digital X-ray image of the examined object. The projection images are then combined using special purpose software for producing a 3-dimensional image volume, which is a 3-dimensional array of voxels, wherein each voxel is essentially a value corresponding to the X-ray attenuation in one point of the real world. The image volume may also be regarded as a stack of layers or slices, wherein each layer or slice is a 2-dimensional image, which can be displayed as normal image. By definition, the layers are oriented essentially orthogonal to the x-ray beams, or in other words such that they are essentially parallel to the projection images. An un-trained viewer may feel that each layer looks like a projection image; despite it is essentially an extraction of structures at a certain depth in the breast. Typically, the thickness of each layer is about 1-5 mm, and the pixel size in each layer is 0.05-0.2 mm. Thus, the voxels are very elongated.

Tomosynthesis has great advantages compared to CT in breast imaging, and many advantages are enabled thanks to the narrow range of projection angles. For example, the examination can be performed simply like a conventional mammography examination, wherein the breast is compressed between a patient support and a compression paddle, which reduces radiation dose and enables better image quality. The drawback of narrow angle range is however a low resolution along the thickness of the breast, which causes thick layers and also causes spill-over between the layers.

Understanding resolution in tomosynthesis may require some efforts. Due to the limited angle, the resolution in thickness direction depends heavily on contour sharpness along the layer plane. According to the well-known Fourier-Slice Theorem, high frequencies in the plane, e.g. small microcalcifications, are well separated into layers, but low frequencies, i.e. large diffuse structures, are spread over several layers. Therefore, the layers outside the breast contain lots of low frequencies from the breast. Thus, layers outside the breast tend to appear as ugly diffuse breast images.

It is important to eliminate the layers outside the breast, since they slow down diagnosis and the work of the radiologists. Speed is crucial in the normal workflow of screening breast imaging, since radiologists look at many images in rapid succession.

Auto-cropping algorithm cannot discard layers solely based on maximum intensity or maximum difference, since the layers outside the breast contain almost as much low frequencies as the layers inside the breast. It may be possible to remove layers, which contain little high frequencies, but such algorithms may fail, in case of imaging certain objects with low contents of contours near the boundary. In addition, avoiding computing the unnecessary layers at all is desirable, as the computational cost is high and proportional to the number of layers. It is believed that reconstruction time will remain a challenge, which is indicated by the amount of published work about parallelism and special hardware for fast reconstruction in tomography tomosynthesis.

Image quality is also a reason for eliminating layers prior to reconstruction. Knowledge of a breast being constrained to a volume provides information to the reconstruction algorithm that there is no X-ray attenuation outside and thus all attenuation is inside the volume. Extra layers make reconstruction more complicated, less stable and call for more regularization, such as low pass filtering. Image volume reconstruction can be regarded a solution to equation system, wherein every layer is a set of unknowns and every projection image is a set of known relations. Some kind of regularization is required if the number of unknowns exceeds the number of the known relations.

In conventional two-dimensional mammography, the breast is compressed between a patient support and a compression paddle. In modern prior art of mammography apparatus design, the compression paddle is movable by a motor, and a position sensor indicates the thickness of the breast, which is used for determining exposure parameters for the X-ray source. In addition, the force of pressure is also measured, which is displayed to the operator or used to control the motor. In addition, the measured force is also used to correct for paddle deflection in the measured thickness.

WO/2001/069533 proposes a method for constraining a 3D model, wherein the method of constraining is based on data from two projection images.

FIG. 1 shows a conventional mammography apparatus 100 for acquisition of two-dimensional X-ray images, according to prior art. The apparatus comprises a compression paddle 140 for compressing a human breast towards a patient support 130. Furthermore, the apparatus comprises a position sensor 270 for measurement of breast thickness, which is the distance between the compression and the patient support. The compression paddle is slightly flexible, and deflects depending on the applied compression force. The mammography apparatus also comprises a force sensor 280, which is used for estimating the deflection and adding a correction term to the value from the position sensor. Yet more, the X-ray apparatus comprises an Automatic Exposure Control (AEC) (not shown), which determines exposure parameters from the breast thickness. Such AEC system is known, for example through WO 2005/077277 for the applicant and incorporated herein through reference. Depending on breast thickness, the X-ray tube 110 of the apparatus is fed by voltages between 25 kV and 40 kV. 120 denotes a collimator arrangement. Other AEC systems are known, for example: M. Åslund, B. Cederström, M. Lundqvist, and M. Danielsson, "AEC for scanning digital mammography based on variation of scan velocity," Medical Physics, 32(11):3367-3374 (2005), and N Perry, M Broeders, C de Wolf, S Tornberg, R Holland, and L von Karsa, editors. European Guidlines for quality assurance in breast cancer screening. Office for Official Publications of the European Communities, Luxembourg, 4 edition, 2006.

SUMMARY OF THE INVENTION

The object of the present invention is to provide an X-ray apparatus for conducting tomosynthesis examination, in particular breast imaging, which outputs and displays only layers containing human tissue, provides improved image quality, is fast and does not spend time for reconstructing layers without human tissue, and does not require that the image field is polluted by any markers or other sharp contours in the compression paddle.

For these reasons, an X-ray apparatus for three-dimensional imaging and in particular for tomosynthesis examination is provided. The present invention is fail-safe removal of layers outside the breast. There is virtually no risk of removing too many layers. The present invention is a cheap solution, which can speed up calculations 2 times for a normal breast of 50 mm, which is half as thick as the maximum breast thickness of 100 mm.

Preferably, the apparatus comprises an x-ray source, an X-ray detector, a compression paddle a position sensor for measuring the position of said compression paddle, a boundary calculator, and a reconstruction means, such as a computer program containing a reconstruction algorithm, such as the EM algorithm or the Lange-Fessler algorithm (1995). The boundary calculator determines which layers to reconstruct, based on values from the position sensor. The reconstruction device shall reconstruct a three-dimensional image volume based on the output from the boundary calculator and the projection images. Preferably, the present invention comprises a force sensor for measurement of the force applied on the compression paddle, and the boundary calculator corrects for the deflection of the compression force depending on the force. The position of the compression paddle is converted to layer index, which is the coordinate system in the reconstruction algorithm. Preferably, the conversion is a division of position over the layer thickness and addition of a constant corresponding to the difference of origin of the different coordinate systems. In case of movable patient support, it is not enough to measure breast thickness. The reconstruction algorithm requires knowledge of the position relative the coordinate system of reconstruction, which is related to the position relative to the X-ray system, i.e. X-ray source and detector and/or collimator in case of a slit scanning system, or most preferably, the position of the phantom, which was used for geometry calibration.

SHORT DESCRIPTION OF THE DRAWINGS

Figure 2:
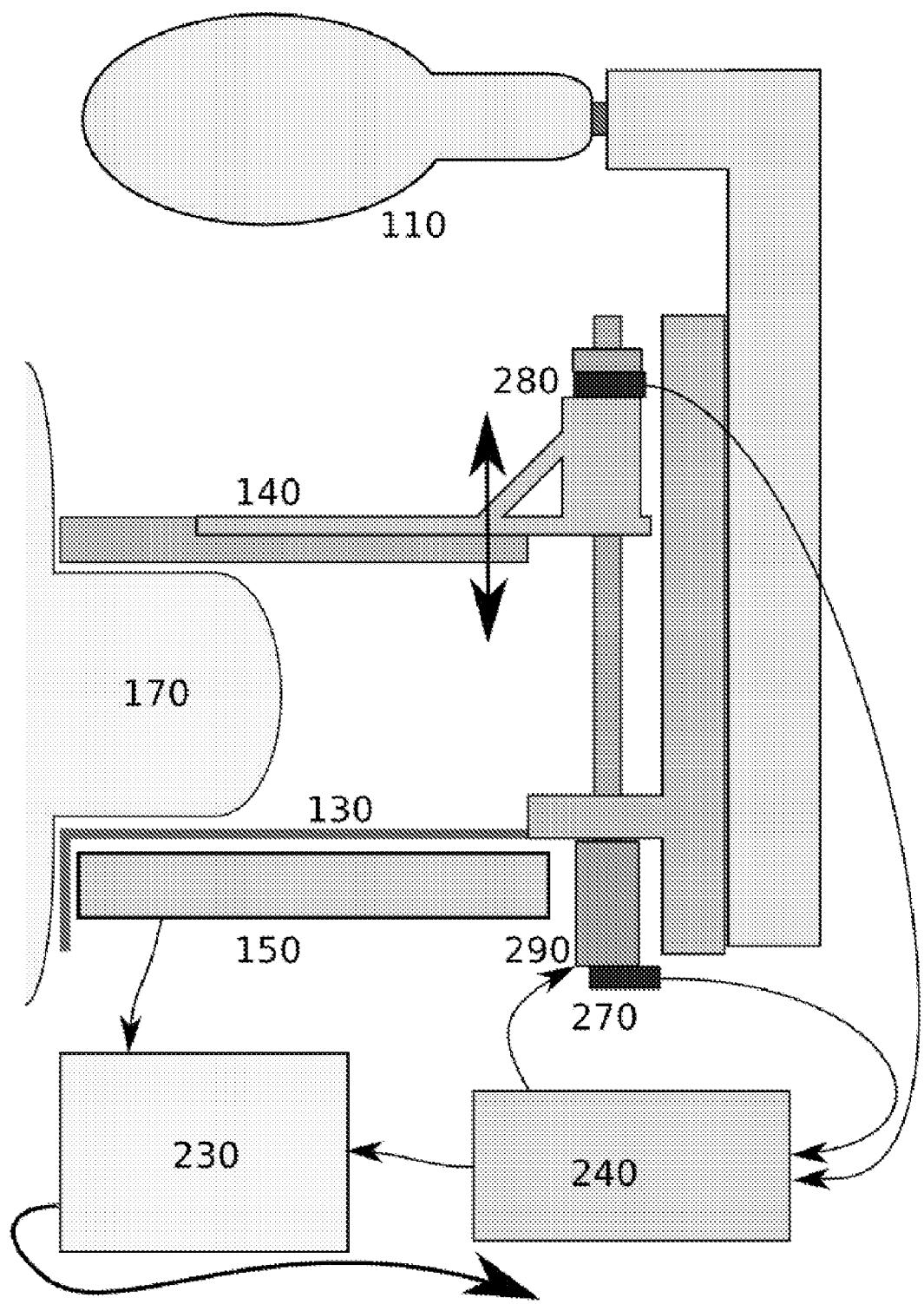

FIG. 1 shows schematically a conventional mammography apparatus for acquisition of two-dimensional X-ray images, and FIG. 2 shows a schematic view of the preferred embodiment of the present invention.

DESCRIPTION OF THE EMBODIMENTS

FIG. 2 shows a preferred embodiment of an x-ray apparatus according to the invention. A human breast 170 is compressed between a patient support 130 and a compression paddle 140 to be irradiated by an X-ray source 110. The detector 150 receives projection images. The detector may be a flat-panel detector or a set of line scanning detectors. The compression paddle 140 is movable by means of an actuator 290 such as a motor and the position is registered by a position sensor 270. A force sensor 280 is arranged to measure the force applied on the compression paddle. The outputs of the position sensor and the force sensors are provided to a boundary calculator 240 which computes the boundary position of the breast as a linear combination of values from the position sensor and an estimate of the deflection, which depends on the force. The deflection depends upon elasticity properties of the compression paddle. In the preferred embodiment, the deflection is close to proportional to the force, and the position of the compression paddle is the sum of the value from the position sensor and a constant multiplied by the compression force. In addition, a second constant is added, since the zero position of the position sensor may deviate from the zero position of the compression paddle. Both constants are calibrated during manufacture or initialization, by pushing the compression paddle towards the patient support or a phantom on the patient support.

In another embodiment of the present invention, the compression paddle deflects according to a curve, which is highly nonlinear with respect to the force, which is handled by computing the deflection using a look-up-table, a second order polynomial, a piecewise linear curve or splines.

In the preferred embodiment, it is possible to switch compression paddles depending on patient and examination, and the apparatus handles different compression paddles using a list of pre-calibrated compression paddles. After switching the compression paddle, the apparatus measures the characteristics of the new compression paddle, in order to identify which compression paddle is attached or to make a new calibration.

In the preferred embodiment, the index of the boundary layer is computed using a quotient of the paddle position over the layer thickness.

In the most preferred embodiment, the boundary calculator is integrated with the controller of the compression actuator and the reconstruction computer. The actuator controller computes the corrected paddle position, which is displayed to the operator. The reconstruction computer determines how many layers to reconstruct, which further depends on the layer thickness.

Furthermore, the embodiment comprises a computing device 230 for reconstruction of a three-dimensional image volume from the projection images. According to the present invention, the reconstruction computer 230 only computes those layers that are inside the breast, as given by the boundary calculator.

In the preferred embodiment, the value from the position sensor or boundary calculator is also used for determining exposure parameters for the X-ray source 110.

There may be many types of position sensors, such as encoders on the motor shaft (not shown), potentiometers in the gear or optical linear scales along the paddle trajectory. Instead of a separate position sensor, it is also possible to use a stepping motor, whereby a motor controller can keep track of the position by counting revolutions of the stepping motor relative to a mechanical position, which may be detected by running the motor until it reaches a mechanical stop and gets stuck. In order to account for all such ways of measuring the compression paddle position, a wider term may be introduced: position gauge.

The measurement is measured relative to the X-ray system. In order to reconstruct the desired volume, the position of the compression paddle relative the X-ray source is known.

In another embodiment of the present invention, the patient support may be arranged movable closer or further away from the X-ray source or detector. In this case the breast is compressed between two movable compression paddles. In such embodiment of the present invention, the positions of both compression paddles are known. It is not enough to know the thickness, as that would lead to reconstruction of an image volume of the right thickness, but partly outside the imaged breast.

The most preferred embodiment is built around a multi-slit scanner, in which the detector and the X-ray source are rotated around a common center of rotation during acquisition of the projection images. For such embodiments, the position sensor measures the position of the compression paddle relative to a point that is still during the irradiation, e.g. the center of rotation.

A side effect of the present invention is to identify phantoms for calibration, depending on their height. Just like in prior art of calibration for 2D slit-scanning mammography, a stair-wedge may be used for calibration of gray-levels. Different stair-wedges may be used for calibration of different exposure parameters. Projection angles may vary, but calibration algorithms multiply the known thickness by a correction factor. In addition, phantoms may contain sharp contours, which may be used in geometry calibration. At that point we may need to know the position of the sharp contours, which may be determined by the position sensor of the compression paddle.

The above mentioned and described embodiments are only given as examples and should not be limiting to the present invention. Other solutions, uses, objectives, and functions within the scope of the invention as claimed in the below described patent claims should be apparent for the person skilled in the art.

I claim:

1. An apparatus for three-dimensional imaging of a human breast comprising a reconstruction means for reconstruction of a three-dimensional image volume representing said human breast, first and a second compression paddles for holding said breast, an actuator for controlling the position at least one of said compression paddles, and a position gauge for measurement of the position of said one compression paddle, wherein said reconstruction means is operatively arranged to receive signals, corresponding to measurements by said position gauge, from said position gauge and constrain a boundary for said image volume based on said received signal.

2. The apparatus according to claim 1, wherein said position gauge comprises a controller connected to said actuator.

3. The apparatus according to claim 1, wherein said position gauge is connected to said actuator for controlling the position of said one compression paddle.

4. The apparatus according to claim 1, further comprising a sensor for measurement of force, and a means for computing said position partly based on said force, whereby said position is corrected for the deflection of said one compression paddle.

5. The apparatus according to claim 1, further comprising an X-ray source and a controller for determining parameters for said X-ray source, based on measurements by said gauge.

6. The apparatus according to claim 1, further comprising an X-ray source for irradiation of said breast, a detector means for receiving X-rays passing through said breast.

7. The apparatus according to claim 6, further comprising an acquisition means for obtaining a set of projection images of said breast, and said reconstruction means is arranged to compute a three-dimensional image volume from said projection images.

8. The apparatus according to claim 6, wherein said position gauge comprises a position sensor or a motor controller.

9. The apparatus according to claim 6, wherein said gauge is operatively arranged to measure the distance relative to a point in said acquisition means.

10. The apparatus according to claim 7, further comprising a controller for controlling parameters in said acquisition means depending on said position gauge.

11. The apparatus according to claim 1, wherein a deflection depending upon elasticity properties of said one compression paddle close to proportional of a force and a position of the one compression paddle is being sum of a value from the position gauge and a constant multiplied by said compression force.

12. The apparatus of claim 11, wherein a second constant is added and both constants are calibrated during manufacturing or initialization, by pushing the one compression paddle towards the patient support on the patient support.

13. The apparatus of claim 1, wherein the one compression paddle deflects according to a pre-determined curve, which is nonlinear with respect to the force, and the deflection is computed using at least one of a look-up-table, a second order polynomial, a piecewise linear curve or lines.

14. The apparatus of claim 1, having exchangeable compression paddles depending on patient and examination.

15. The apparatus of claim 14, wherein said apparatus is arranged to handle different compression paddles using a list of pre-calibrated compression paddles.

16. The apparatus of claim 15, wherein after switching a compression paddle, the apparatus is arranged to measure characteristics of the new compression paddle, in order to identify which compression paddle is attached or to make a new calibration.

17. The apparatus of claim 1, an index of the boundary layer is computed using a quotient of the paddle position over a layer thickness.

18. The apparatus of claim 1, comprising a boundary calculator.

19. The apparatus of claim 18, wherein said boundary calculator is integrated with a controller of a compression actuator and the reconstruction computer.

20. The apparatus of claim 19, wherein the actuator controller computes a corrected paddle position, displayable to an operator.

21. The apparatus of claim 19, wherein the reconstruction computer determines the number of the layers to reconstruct, which further depends on the layer thickness.

22. A reconstruction device for reconstruction of a three-dimensional image volume from a set of projection images of a human body part, said device being connected to a position gauge for measurement of the position of a first and a second compression paddle for compressing said body part, wherein said reconstruction device is operatively arranged to receive signals, corresponding to measurements by said position gauge representing a distance between said first and second paddles, from said position gauge and constrain a boundary for said image based on said received signal.

23. An apparatus for three-dimensional imaging of a human breast comprising a reconstruction means for reconstruction of a three-dimensional image volume, a first and a second compression paddle for holding said breast, an actuator for controlling the position of at least one of said compression paddle, and a position gauge for measurement of the position of said one compression paddle, an acquisition means for obtaining a set of projection images of said breast, and said reconstruction means being operatively arranged to compute a three-dimensional image volume from the combination of said projection images and a value from said position gauge corresponding to distance of said first and second position paddles.

24. A method for obtaining a three-dimensional breast image, comprising the steps of measuring a position of a movable first and second compression paddles holding said breast, acquiring a set of projection images, and reconstructing a three-dimensional image volume from said projection images, said step of reconstructing further involving constraining a boundary of said image based on a value from a position gauge corresponding to a distance between said first and second paddle.

25. The method according to claim 24, wherein said position gauge comprises a position sensor or a motor controller.

26. A computer readable medium encoded with a computer program for obtaining a three-dimensional breast image, said program comprising a set of instructions for receiving the measured positions of a movable compression paddle holding said breast between said compression paddle and another surface, a set of instructions for receiving a set of projection images, a set of instructions for reconstructing a three-dimensional image volume from said projection images, said set of instructions for reconstructing further comprising instructions for constraining a boundary of said image based on a value from a position gauge corresponding to a distance between said paddle and said surface.

* * * * *